United States Patent
Fornoni et al.

(10) Patent No.: US 11,344,604 B2
(45) Date of Patent: May 31, 2022

(54) METHOD FOR TREATING KIDNEY DISORDERS

(71) Applicant: UNIVERSITY OF MIAMI, Miami, FL (US)

(72) Inventors: Alessia Fornoni, Miami, FL (US); Sandra Merscher, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 17/259,883

(22) PCT Filed: Jul. 12, 2019

(86) PCT No.: PCT/US2019/041730
§ 371 (c)(1),
(2) Date: Jan. 12, 2021

(87) PCT Pub. No.: WO2020/014690
PCT Pub. Date: Jan. 16, 2020

(65) Prior Publication Data
US 2021/0275632 A1    Sep. 9, 2021

Related U.S. Application Data

(60) Provisional application No. 62/697,556, filed on Jul. 13, 2018.

(51) Int. Cl.
*A61K 38/17* (2006.01)
*A61P 13/12* (2006.01)
*C07K 14/775* (2006.01)

(52) U.S. Cl.
CPC .......... *A61K 38/1709* (2013.01); *A61P 13/12* (2018.01); *C07K 14/775* (2013.01)

(58) Field of Classification Search
CPC ..... A61K 38/1709; A61K 38/17; A61P 13/12; C07K 14/775
See application file for complete search history.

(56) References Cited

U.S. PATENT DOCUMENTS

| | | | |
|---|---|---|---|
| 5,496,807 A | 3/1996 | Marchi et al. | |
| 6,114,123 A * | 9/2000 | Murry | C07K 14/775 435/252.3 |
| 7,030,146 B2 | 4/2006 | Baynes et al. | |
| 9,592,268 B2 * | 3/2017 | Hla | A61K 38/1709 |
| 2019/0185545 A1 * | 6/2019 | Hla | A61P 9/10 |

FOREIGN PATENT DOCUMENTS

| WO | 2018/051298 A1 | 3/2018 |
|---|---|---|
| WO | 2018/052615 A1 | 3/2018 |

OTHER PUBLICATIONS

Chronic Kidney Disease from Merck Manual, pp. 1-5. Accessed Jan. 19, 2022. (Year: 2022).*
Alport Syndrome from Merck Manual, pp. 1-3. Accessed Jan. 19, 2022. (Year: 2022).*
Axler et al., Apolipoprotein M associates to lipoproteins through its retained signal peptide, FEBS Lett, 582(5):826-828 (2008).
Bosteen et al., Effects of apolipoprotein M in uremic atherosclerosis, Atherosclerosis, 265:93-101 (2017).
Charbit et al., Cyclosporin therapy in patients with Alport syndrome, Pediatric Nephrology, 22(1):57-63 (2007).
Dahlback et al., Apolipoprotein M—a novel player in high-density lipoprotein metabolism and atherosclerosis, Current Opinion in Lipidology, 17(3):291-295 (2006).
Giunti et al., Diabetic nephropathy: from mechanisms to rational therapies, Minerva Medica, 97(3):241-262 (2006).
International Application No. PCT/US19/41730, International Preliminary Report on Patentability, dated Jan. 28, 2021.
International Application No. PCT/US19/41730, International Search Report and Written Opinion, dated Sep. 27, 2019.
Sorensen et al., Apolipoprotein M in patients with chronic kidney disease, Atherosclerosis, 275:304-311 (2018).
Willams et al., The next generation of diabetic nephropathy therapies: an update, Advances in Chronic Kidney Disease, 12(2):212-222 (2005).
Wolfrum et al., Apolipoprotein M is required for prebeta-HDL formation and cholesterol efflux to HDL and protects against atherosclerosis, Nature Medicine, 11(4):418-442 (2005).
Zhang et al.. Specific tissue expression and cellular localization of human apolipoprotein M as determined by in situ hybridization, Acta Histochemica, 105(1):67-72 (2003).
Christoffersen, et al., "ApoB and apoM—New aspects of lipoprotein biology in uremia-induced atherosclerosis", European Journal of Pharmacology, 816:154-160 (2017).
Hajny et al., "A Novel Perspective on the ApoM-S1P Axis, Highlighting the Metabolism of ApoM and Its Role in Liver Fibrosis and Neuroinflammation", International Journal of Molecular Sciences, vol. 18, pp. 1-19 (2017).
Hu et al., "Characteristics of apolipoprotein M and its relation to atherosclerosis and diabetes", Biochimica et Biophysica Acta, 1801:100-105 (2010).
Zhang et al., "ApoM/HDL-C and apoM/apoA-I ratios are indicators of diabetic nephropathy in health controls and type 2 diabetes mellitus", Clinica Chimica Acta, 466:31-37 (2017).

* cited by examiner

*Primary Examiner* — Julie Ha
(74) *Attorney, Agent, or Firm* — Marshall, Gerstein & Borun LLP

(57) ABSTRACT

Disclosed herein is a method of treating or preventing renal disease in a subject suffering from Alport Syndrome, as well a method of treating or preventing chronic kidney disease. The method comprises administering to a subject in need thereof an effective amount of human apolipoprotein M.

3 Claims, 7 Drawing Sheets
Specification includes a Sequence Listing.

MFHQIWAALL YFYGIILNSI YQCPEHSQLT TLGVDGKEFP EVHLGQWYFI
AGAAPTKEEL ATFDPVDNIV FNMAAGSAPM QLHLRATIRM KDGLCVPRKW
IYHLTEGSTD LRTEGRPDMK TELFSSSCPG GIMLNETGQG YQRFLLYNRS
PHPPEKCVEE FKSLTSCLDS KAFLLTPRNQ EACELSNN (SEQ ID NO: 1)

FIG. 4 caacagagca ccagcttccc tcctgccctg aagatgttcc accaaatttg ggcagctctg ctctacttct atggtattat
ccttaactcc atctaccagt gccctgagca cagtcaactg acaactctgg gcgtggatgg gaaggagttc ccagaggtcc
acttgggcca gtggtacttt atcgcagggg cagctcccac caaggaggag ttggcaactt tgaccctgt ggacaacatt
gtcttcaata tggctgctgg ctctgccccg atgcagctcc accttcgtgc taccatccgc atgaaagatg ggctctgtgt
gccccggaaa tggatctacc acctgactga agggagcaca gatctcagaa ctgaaggccg ccctgacatg aagactgagc
tcttttccag ctcatgccca ggtggaatca tgctgaatga gacaggccag ggttaccagc gctttctcct ctacaatcgc
tcaccacatc ctcccgaaaa gtgtgtggag gaattcaagt ccctgacttc ctgcctggac tccaaagcct tcttattgac
tcctaggaat caagaggcct gtgagctgtc caataactga cctgtaactt catctaagtc cccagatggg tacaatggga
gctgagttgt tggagggaga agctggagac ttccagctcc agctcccact caagataata aagataattc ttcaatcctc
aaaaaaaaaa aaaa (SEQ ID NO: 2)

FIG. 5

SEQUENCE LISTING

<160> NUMBER OF SEQ ID NOS: 9

<210> SEQ ID NO 1
<211> LENGTH: 188
<212> TYPE: PRT
<213> ORGANISM: Homo Sapiens

<400> SEQUENCE: 1

Met Phe His Gln Ile Trp Ala Ala Leu Leu Tyr Phe Tyr Gly Ile Ile
1               5                   10                  15

Leu Asn Ser Ile Tyr Gln Cys Pro Glu His Ser Gln Leu Thr Thr Leu
            20                  25                  30

Gly Val Asp Gly Lys Glu Phe Pro Glu Val His Leu Gly Gln Trp Tyr
        35                  40                  45

Phe Ile Ala Gly Ala Ala Pro Thr Lys Glu Glu Leu Ala Thr Phe Asp
    50                  55                  60

Pro Val Asp Asn Ile Val Phe Asn Met Ala Ala Gly Ser Ala Pro Met
65                  70                  75                  80

Gln Leu His Leu Arg Ala Thr Ile Arg Met Lys Asp Gly Leu Cys Val
                85                  90                  95

Pro Arg Lys Trp Ile Tyr His Leu Thr Glu Gly Ser Thr Asp Leu Arg
            100                 105                 110

Thr Glu Gly Arg Pro Asp Met Lys Thr Glu Leu Phe Ser Ser Ser Cys
        115                 120                 125

Pro Gly Gly Ile Met Leu Asn Glu Thr Gly Gln Gly Tyr Gln Arg Phe
    130                 135                 140

Leu Leu Tyr Asn Arg Ser Pro His Pro Pro Glu Lys Cys Val Glu Glu
145                 150                 155                 160

Phe Lys Ser Leu Thr Ser Cys Leu Asp Ser Lys Ala Phe Leu Leu Thr
                165                 170                 175

Pro Arg Asn Gln Glu Ala Cys Glu Leu Ser Asn Asn
            180                 185

<210> SEQ ID NO 2
<211> LENGTH: 734
<212> TYPE: DNA
<213> ORGANISM: Homo Sapiens

<400> SEQUENCE: 2
caacagagca ccagcttccc tcctgccctg aagatgttcc accaaatttg ggcagctctg      60
ctctacttct atggtattat ccttaactcc atctaccagt gccctgagca cagtcaactg     120
acaactctgg gcgtggatgg gaaggagttc ccagaggtcc acttgggcca gtggtacttt     180
atcgcagggg cagctcccac caaggaggag ttggcaactt tgaccctgt ggacaacatt      240 gtcttcaata tggctgctgg ctctgccccg atgcagctcc accttcgtgc taccatccgc     300
atgaaagatg gctctgtgt gccccggaaa tggatctacc acctgactga agggagcaca      360
gatctcagaa ctgaaggccg ccctgacatg aagactgagc tcttttccag ctcatgccca     420
ggtggaatca tgctgaatga cagggccag ggttaccagc gctttctcct ctacaatcgc      480
tcaccacatc ctcccgaaaa gtgtgtggag gaattcaagt ccctgacttc ctgcctggac     540
tccaaagcct tcttattgac tcctaggaat caagaggcct gtgagctgtc caataactga     600
cctgtaactt catctaagtc cccagatggg tacaatggga gctgagttgt tggagggaga     660
agctggagac ttccagctcc agctcccact caagataata aagataattc ttcaatcctc     720
aaaaaaaaaa aaaa                                                       734

<210> SEQ ID NO 3

<400> SEQUENCE: 3

000

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
cgtttccggg aagtgtccta                                               20

<210> SEQ ID NO 5
<211> LENGTH: 24
<212> TYPE: DNA
<213> ORGANISM: Artificial Sequence
<220> FEATURE:
<223> OTHER INFORMATION: Synthetic Primer

<400> SEQUENCE: 5
gctagagatg acaaggagga tgga                                          24

<210> SEQ ID NO 6
<211> LENGTH: 25
<212> TYPE: DNA
<213> ORGANISM: Artificial Sequence
<220> FEATURE:
<223> OTHER INFORMATION: Synthetic Primer

<400> SEQUENCE: 6
aggtctcagc cttctaaagt tcctc                                         25

<210> SEQ ID NO 7
<211> LENGTH: 26
<212> TYPE: DNA
<213> ORGANISM: Artificial Sequence
<220> FEATURE:
<223> OTHER INFORMATION: Synthetic Primer

<400> SEQUENCE: 7
tctctcgaag tgaatgaaat ttatcg                                        26

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
cctgggcctg tggtacttta                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

```
<400> SEQUENCE: 9
ccatgtttcc tttcccttca                                                    20
```

METHOD FOR TREATING KIDNEY DISORDERS

CROSS REFERENCE TO RELATED APPLICATIONS AND INCORPORATION BY REFERENCE OF MATERIAL SUBMITTED ELECTRONICALLY

This application claims the benefit of U.S. Provisional Patent Application No. 62/697,556, filed Jul. 13, 2018, the entire contents of which are fully incorporated herein by reference.

FIELD OF THE INVENTION

The present disclosure relates to materials and methods of treating chronic kidney disease and renal disease in subjects suffering from Alport Syndrome.

A Sequence Listing, which is a part of the present disclosure, is submitted concurrently with the specification as a text file. The name of the text file containing the Sequence Listing is "53188_Seqlisting.txt." The Sequence Listing was created on Jul. 2, 2019, and is 4,142 bytes in size. The subject matter of the Sequence Listing is incorporated herein by reference.

BACKGROUND

Alport Syndrome is an inherited disease caused by mutations in three collagen type IV genes, COL4A3, COL4A4, and COL4A5. The disease is characterized by progressive renal failure, hypertension, proteinuria, greatly increased risk of cardiovascular disease, and loss of hearing and vision. Current therapy for Alport Syndrome is aimed at ameliorating the symptoms and includes angiotensin-converting enzyme (ACE) inhibitors or angiotensin receptor blockers (ARB). Such treatments only slow the loss of kidney function or manage blood pressure and do not treat or prevent the other effects of the disease.

There remains a need for therapeutic options for renal impairment associated with Alport Syndrome and other Col4-related diseases, as well as therapeutic options for chronic kidney diseases in general.

SUMMARY

In one aspect, described herein is a method of treating or preventing chronic kidney disease in a subject. The method comprises administering human apolipoprotein M (rhAPOM) to the subject in an amount effective to treat chronic kidney disease in the subject.

In another aspect, described herein is a method of treating or preventing renal disease in a subject suffering from Alport Syndrome. The method comprises administering recombinant human apolipoprotein M to the subject in an amount effective to treat renal disease in the subject.

In yet another aspect, described herein is human apolipoprotein M for use in the treatment or prevention of chronic kidney disease or renal disease associated with Alport Syndrome, wherein the human apolipoprotein M is administered in an amount and with a dosage regime effective to treat or prevent the chronic kidney disease or renal disease.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. The terms "comprising," "having," "including," and "containing" are to be construed as open-ended terms unless otherwise noted. If aspects of the invention are described as "comprising" a feature, embodiments also are contemplated "consisting of" or "consisting essentially of" the feature. The use of any and all examples, or exemplary language (e.g., "such as") provided herein, is intended merely to better illustrate the disclosure and does not pose a limitation on the scope of the disclosure unless otherwise claimed. No language in the specification should be construed as indicating any non-claimed element as essential to the practice of the disclosure. Other than in the operating examples, or where otherwise indicated, all numbers expressing quantities of ingredients or reaction conditions used herein should be understood as modified in all instances by the term "about" as that term would be interpreted by the person skilled in the relevant art.

BRIEF DESCRIPTION OF THE FIGURES

FIG. 4 is a human APOM amino acid sequence.

FIG. 5 is a human APOM nucleic acid sequence.

DETAILED DESCRIPTION

Figure 1A:
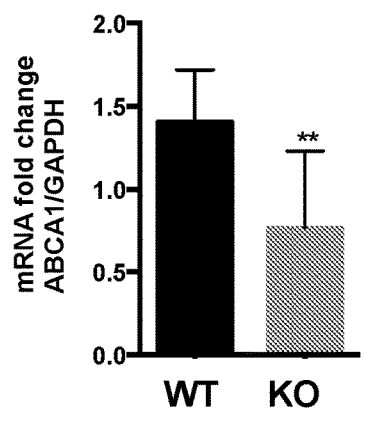
FIGS. 1A-1C: Decreased expression of ABCA1, ABCG1 and APOM in glomeruli from Col4a3 knockout mice. Bar graph analysis of mRNA expression by quantitative real-time PCR demonstrating decreased expression of ABCA1 (A), ABCG1 (B) and APOM (C) in glomeruli isolated from Col4a3 knockout mice (KO) when compared to wildtype controls (WT). $p<0.01$, *$p<0.001$.

The present disclosure provides a method of treating or preventing renal disease in a subject in need thereof suffering from Alport Syndrome and a method of treating chronic kidney disease in a subject in need thereof. The method comprises administering a therapeutically effective amount of human apolipoprotein M (APOM) to the subject. The present disclosure further provides human apolipoprotein M for use in the treatment or prevention of renal disease associated with Alport Syndrome, as well as chronic kidney disease.

The terms "treating" and "treatment" refer to any improvement in the disease or symptoms of the disease being treated. As such, "treating" and "treatment" includes complete elimination of one or more symptoms of the disease, but this is not required. One of ordinary skill in the art will appreciate that any degree of amelioration of a renal disorder or symptom associated therewith is beneficial to a subject, such as a human patient. The quality of life of a patient is improved by reducing to any degree the severity of symptoms in a subject. The terms "preventing" or "prevention" refer to inhibiting the disorder, delaying the onset of disease, or delaying the appearance of one or more symptoms of the disease. "Prevention" does not require 100% inhibition of disease onset, although this is contemplated.

Apolipoprotein M

Apolipoprotein M (APOM) is an apolipoprotein and member of the lipocalin protein family. The lipocalins share limited regions of sequence homology and a common tertiary structure architecture. They have an eight-stranded, antiparallel, symmetrical-barrel fold, which is in essence a beta sheet which has been rolled into a cylindrical shape housing a ligand binding site. Lipocalins have been associated with many biological processes, among them immune responses, pheromone transport, biological prostaglandin synthesis, retinoid binding, and cancer cell interactions. APOM is associated with high density lipoproteins and to a lesser extent with low density lipoproteins and triglyceride-rich lipoproteins. APOM is involved in lipid transport and can bind sphingosine-1-phosphate, myristic acid, palmitic acid and stearic acid, retinol, all-trans-retinoic acid and 9-cis-retinoic acid. APOM is further described in, e.g., Zhang et al., Acta Histochemica, 2003; 105(1): 67-72; Axler et al., FEBS Lett. 2008 March 5;582(5):826-8.

The amino acid sequence of human APOM is provided as SEQ ID NO: 1. In various aspects, the human APOM comprises an amino acid sequence at least 90% identical (e.g., at least 95%, at least 99%, or 100% identical) to SEQ ID NO: 1. Alternatively, the APOM is encoded by the nucleic acid sequence of SEQ ID NO: 2. In various aspects, the full length APOM protein is not required. Optionally, the APOM is fused to a moiety that improves half life or another pharmacokinetic property of the protein. For example, in one embodiment, APOM is fused with the Fc region of an antibody, such as an IgG1 antibody. Indeed, in a preferred embodiment, the human APOM comprises Met-1 through Asn-188 of the amino acid sequence of SEQ ID NO: 1 fused to the Fc region of an IgG1.

Recombinant APOM may be produced using methods known in the art.

Renal Disease

In one aspect, the disclosure provides a method of treating renal disease in a subject in need thereof suffering from Alport Syndrome. As such, in certain embodiments, the subject has been diagnosed as having Alport Syndrome prior to administration of human recombinant apolipoprotein M. Diagnosis of Alport Syndrome may be achieved through evaluation of parameters including, without limitation, a subject's family history, clinical features (including without limitation proteinuria, albuminuria, hematuria, impaired GFR, deafness and/or ocular changes) and results of tissue biopsies. Kidney biopsies may be tested for the presence or absence of the type IV collagen alpha-3, alpha-4, and alpha-5 chains. Additionally, structural changes in the glomerulus can be detected by electron microscopy of kidney biopsy material. A skin biopsy may be tested for the presence of the type IV collagen alpha-5 chain, which is normally present in skin and almost always absent from male subjects with the X-linked form of Alport Syndrome. Diagnosis of Alport Syndrome may also include screening for mutations in one or more of the Col4a3, Col4a4, or Col4a5 genes.

The term "renal disease" or "kidney disease" as used herein means any alteration in normal physiology and function of the kidney. This term includes but is not limited to conditions such as nephropathy; primary glomerulopathies (focal segmental glomerulosclerosis), Minimal Change disease, Membranous GN, IgA Nephropathy; Glomerulonephritis; polycystic kidney disease; acute and chronic interstitial nephritis, Mesoamerican Nephropathy, nephromegaly (extreme hypertrophy of one or both kidneys); nephrotic syndrome; nephritic syndrome, end stage renal disease (ESRD); acute and chronic renal failure; interstitial disease; nephritis; sclerosis, an induration or hardening of tissues and/or vessels resulting from causes that include, for example, inflammation due to disease or injury; renal fibrosis and scarring; renal-associated proliferative disorders; and other primary or secondary nephrogenic conditions.

The term "chronic kidney disease (CKD)" as used herein is defined as abnormalities of kidney structure or function, present for more than three months, with implications for health. CKD has been classified according to the National Kidney Foundation as comprising 5 stages: stage 1 is kidney damage with normal eGFR (mL/min/1.73 m$^2$) of 90 or above; stage 2 is kidney damage with a mild decrease in GFR (GFR 60-89 mL/min/1.73 m$^2$); stage 3 is a moderate decrease in GFR (GFR 30-59 mL/min/1.73 m$^2$); stage 4 is a severe decrease in GFR (GFR 15-29 mL/min/1.73 m$^2$); and stage 5 is kidney failure (GFR<15 mL/min/1.73 m$^2$ or dialysis). Stage 3 has been subdivided into stage 3A, which is a mild to moderate decrease in GFR (GFR 45-59), and stage 3B, which is a moderate to severe decrease in GFR (GFR 30-44).

Renal diseases or kidney diseases may also be generally defined as a "nephropathy" or "nephropathies." The terms "nephropathy" or "nephropathies" encompass all clinical-pathological changes in the kidney which may result in kidney fibrosis and/or glomerular diseases (e.g., glomerulosclerosis or glomerulonephritis) and/or chronic renal insufficiency, and can cause end stage renal disease and/or renal failure. Some aspects of the present disclosure relate to the prevention and/or treatment of hypertensive nephropathy, diabetic nephropathy, and other types of nephropathy such as analgesic nephropathy, immune-mediated glomerulopathies (e.g., IgA nephropathy or Berger's disease, lupus nephritis), ischemic nephropathy, HIV-associated nephropathy, membranous nephropathy, glomerulonephritis, glomerulosclerosis, radiocontrast media-induced nephropathy, toxic nephropathy, analgesic-induced nephrotoxicity, cisplatin nephropathy, transplant nephropathy, and other forms of glomerular abnormality or injury, or glomerular capillary injury (tubular fibrosis). In some embodiments, the terms "nephropathy" or "nephropathies" refer specifically to a disorder or disease where there is either the presence of proteins (i.e., proteinuria) in the urine of a subject and/or the presence of renal insufficiency.

In some embodiments, the subject is suffering from albuminuria or proteinuria. Exemplary disorders associated with albuminuria include, but are not limited to, chronic kidney disease, proliferative glomerulonephritis (e.g., immunoglobulin A nephropathy, membranoproliferative glomerulonephritis, mesangial proliferative glomerulonephritis, anti-GBM disease, renal vasculitis, lupus nephritis, cryoglobulinemia-associated glomerulonephritis, bacterial endocarditis, Henoch-Schonlein purpura, postinfectious glomerulonephritis, or hepatitis C), and nonproliferative glomerulonephritis (e.g., membranous glomerulonephritis, minimal-change disease, primary focal segmental glomerulosclerosis (FSGS), fibrillary glomerulonephritis, immunotactoid glomerulonephritis, amyloidosis, hypertensive nephrosclerosis, light-chain disease from multiple myeloma and secondary focal glomerulosclerosis).

In any of the embodiments provided herein, a subject may be subjected to certain tests to evaluate kidney function. Such tests include, without limitation, measurement of blood urea nitrogen in the subject; measuring creatinine in the blood of the subject; measuring creatinine clearance in the blood of the subject; measuring proteinuria in the subject; measuring albumin:creatinine ratio in the subject; measuring glomerular filtration rate in the subject; and measuring urinary output in the subject. In various aspects, the method of the disclosure improves the outcome of one or more of these tests in a subject suffering from a renal disorder described herein.

In any of the embodiments provided herein, proteins present in the urine or blood may be used to evaluate kidney function. Such tests of kidney function include, but are not limited to, measuring albumin/creatinine urinary ratios, total protein/creatinine urinary ratios, albumin or total proteins in timed urinary collections, N-acetyl-(3-D-glucosaminidase (NAG) protein in the urine of the subject; measuring neutrophil gelatinase-associated lipocalin (NGAL) protein in the urine of the subject; measuring kidney injury molecule-1 (KIM-1) protein in the urine of the subject; measuring interleukin-18 (IL-18) protein in the urine of the subject; measuring connective tissue growth factor (CTGF) levels in the urine of the subject; measuring monocyte chemoattractant protein 1 (MCP1) levels in the urine of the subject; measuring collagen IV (Col IV) fragments in the urine of the subject; measuring collagen III (Col III) fragment levels in the urine of the subject; measuring cystatin C protein in the blood of a subject; measuring (3-trace protein (BTP) in the blood of a subject; and measuring 2-microglobulin (B2M) in the blood of a subject. In any of the embodiments provided herein, markers of podocyte injury can be measuring in the urine. Such proteins include nephrin and podocin. The proteins may be quantitated, for example, by enzyme-linked immunosorbent assay (ELISA), or radioimmunoas say (RIA) using commercially available kits.

Timing of Administration and Dosage

In some embodiments, one or more administrations of human apolipoprotein M are carried out over a therapeutic period of, for example, about 1 week to about 18 months (e.g., about 1 month to about 12 months, about 1 month to about 9 months or about 1 month to about 6 months or about 1 month to about 3 months). In some embodiments, a subject is administered one or more doses of human apolipoprotein M described herein over a therapeutic period of, for example, about 1 month to about 12 months (52 weeks) (e.g., about 2 months, about 3 months, about 4 months, about 5 months, about 6 months, about 7 months, about 8 months, about 9 months, about 10 months, or about 11 months).

In addition, it may be advantageous to administer multiple doses of the human apolipoprotein M or separate the administration of doses in time, depending on the therapeutic regimen selected for a particular human subject. In some embodiments, the human apolipoprotein M is administered periodically over a time period of one year (12 months, 52 weeks) or less (e.g., 9 months or less, 6 months or less, or 3 months or less). In this regard, human apolipoprotein M is optionally administered to the human once every about 3 days, or about 7 days, or about 2 weeks, or about 3 weeks, or about 4 weeks, or about 5 weeks, or about 6 weeks, or about 7 weeks, or about 8 weeks, or about 9 weeks, or about 10 weeks, or about 11 weeks, or about 12 weeks, or about 13 weeks, or about 14 weeks, or about 15 weeks, or about 16 weeks, or about 17 weeks, or about 18 weeks, or about 19 weeks, or about 20 weeks, or about 21 weeks, or about 22 weeks, or about 23 weeks, or about 6 months, or about 12 months.

In some embodiments, a dose of human apolipoprotein M comprises between about 1 to about 500 milligrams (e.g., between about 1 to about 400 milligrams or about 3 to about 300 milligrams) of human apolipoprotein M per kilogram of body weight (mg/kg). For example, the dose of human apolipoprotein M may comprise at least about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, or about 49 mg/kg, or about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 125 mg/kg, about 150 mg/kg, about 175 mg/kg, about 200 mg/kg, about 225 mg/kg, about 250 mg/kg, about 275 mg/kg, about 300 mg/kg, about 325 mg/kg, about 350 mg/kg, about 375 mg/kg, about 400 mg/kg, about 450 mg/kg, or about 500 mg/kg of human apolipoprotein M. Ranges between any and all of these endpoints are also contemplated, e.g., about 1 mg/kg to about 100 mg/kg, about 3 mg/kg to about 300 mg/kg, about 3 mg/kg to about 100 mg/kg, about 5 mg/kg to about 50 mg/kg, about 3 mg/kg to about 75 mg/kg, about 1 mg/kg to about 50 mg/kg, about 100 mg/kg to about 300 mg/kg, about 50 mg/kg to about 200 mg/kg, or about 200 mg/kg to about 300 mg/kg.

Pharmaceutical Compositions

In some embodiments, human apolipoprotein M is formulated as a composition together with a pharmaceutically effective diluent, carrier, solubilizer, emulsifier, preservative, and/or adjuvant. Pharmaceutical compositions include, but are not limited to, liquid, frozen, and lyophilized compositions.

Preferably, formulation materials are nontoxic to recipients at the dosages and concentrations employed. In specific embodiments, pharmaceutical compositions comprising a therapeutically effective amount of human apolipoprotein M are provided.

In some embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

Combination Therapies

In some embodiments, the methods described herein comprise administering another agent for preventing or treating a renal disorder such as nephropathy, or an associated disorder or complication. Examples of such known compounds include but are not limited to: ACE inhibitor drugs (e.g., captopril (Capoten®), enalapril (Innovace®), fosinopril (Staril®), lisinopril (Zestril®), perindopril (Coversyl®), quinapril (Accupro®), trandanalopril (Gopten®), lotensin, moexipril, ramipril); RAS blockers; angiotensin receptor blockers (ARBs) (e.g., Olmesartan, Irbesartan, Losartan, Valsartan, candesartan, eprosartan, telmisartan, etc); protein kinase C (PKC) inhibitors (e.g., ruboxistaurin); inhibitors of AGE-dependent pathways (e.g., aminoguanidine, ALT-946, pyrodoxamine (pyrododorin), OPB-9295, alagebrium); anti-inflammatory agents (e.g., clyclooxigenase-2 inhibitors, mycophenolate mophetil, mizoribine, pentoxifylline), GAGs (e.g., sulodexide (U.S. Pat. No. 5,496,807)); pyridoxamine (U.S. Pat. No. 7,030,146); endothelin antagonists (e.g., SPP 301), COX-2 inhibitors, PPAR-γ antagonists and other compounds like amifostine (used for cisplatin nephropathy), captopril (used for diabetic nephropathy), cyclophosphamide (used for idiopathic membranous nephropathy), sodium thiosulfate (used for cisplatin nephropathy), tranilast, etc. (Williams and Tuttle (2005), Advances in Chronic Kidney Disease, 12 (2):212-222; Giunti et al. (2006), Minerva *Medica,* 97:241-62).

Additionally, the methods described herein may also include co-administration of at least one other therapeutic agent for the treatment of another disease directly or indirectly related to renal disorder complications, including but not limited to: dyslipidemia, hypertension, obesity, neuropathy, inflammation, and/or retinopathy. Such additional therapeutic agents include, but are not limited to, corticosteroids; immunosuppressive medications; antibiotics; antihypertensive and diuretic medications (such as thiazide diuretics and ACE-inhibitors or (3-adrenergic antagonists); lipid lowering agents such as bile sequestrant resins, cholestyramine, colestipol, nicotinic acid, and more particularly drugs and medications used to reduce cholesterol and triglycerides (e.g., fibrates (e.g., Gemfibrozil®) and HMG-CoA inhibitors such as Lovastatin®, Atorvastatin®, Fluvastatin®, Lescol®, Lipitor®, Mevacor®, Pravachol®, Pravastatin®, Simvastatin®, Zocor®, Cerivastatin®, etc); nicotinic acid; and Vitamin D.

Additional examples of agents that can be co-administered with human apolipoprotein M include immunomodulating agents or immunosuppressants (such as those that are used by subjects who have received a kidney transplant (e.g., when they have developed a nephropathy), anti-obesity agents, and appetite reducers (including, but not limited to, Xenical™ (Roche), Meridia™ (Abbott), Acomplia™ (Sanofi-Aventis), and sympathomimetic phentermine), agents that are used to treat hyperkalemia and/or to reduce the risk of ventricular fibrillation caused by hyperkalemia (e.g., calcium gluconate, insulin, sodium bicarbonate, $\beta_2$-selective catacholamine such as salbutamol (albuterol, Ventolin®), and polystyrene sulfonate (Calcium Resonium, Kayexalate)) and patiromer (Veltassa®).

As used herein, the term "concomitant" or "concomitantly" as in the phrases "concomitant therapeutic treatment" or "concomitantly with" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g., a human). Preferably the first agent is human recombinant apolipoprotein M or a composition containing human recombinant apolipoprotein M. The second agent may be selected from the other therapeutics described herein.

EXAMPLE

This Example demonstrates that administration of APOM to a clinically relevant in vivo model of Alport Syndrome protects against renal failure, as well as abnormal lipid content in kidney cortexes.

Materials and Methods:

Human recombinant APOM protein construction and use: The protein was purchased from Sino Biological (13495-H02H). A DNA sequence encoding human APOM protein (O95445) (Met 1-Asn 188) was fused with the Fc region of human IgG1 at the C-terminus. The resulting human recombinant APOM protein was found to be >85% pure as determined by SDS-PAGE with an endotoxin concentration of <1.0 EU perm of the protein as determined by the LAL method.

Formulation: The protein was lyophilized from sterile PBS, pH 7.4 and normally 5%-8% trehalose, mannitol and 0.01% Tween 80 was added as protectants before lyophilization. Specific concentrations were included in the hardcopy of each COA. For injection, sterile water was added to the vial to prepare a stock solution of 0.25 mg/ml.

```
Human APOM protein sequence: O95445 (1-188):
                                       (SEQ ID NO: 1)
MFHQIWAALL YFYGIILNSI YQCPEHSQLT TLGVDGKEFP

EVHLGQWYFI AGAAPTKEEL ATFDPVDNIV FNMAAGSAPM

QLHLRATIRM KDGLCVPRKW IYHLTEGSTD LRTEGRPDMK

TELFSSSCPG GIMLNETGQG YQRFLLYNRS PHPPEKCVEE

FKSLTSCLDS KAFLLTPRNQ EACELSNN.
```

Enzyme-linked immunosorbent assay (ELISA) for APOM: The mouse-APOM ELISA was purchased from LSBio (#LS-F21415) and APOM protein concentrations in serum, urine and lysates were determined following the manufacturer's protocol.

S1P assay kit: The S11) assay kit was purchased from Echelon (#K-1900) and S1Ps concentrations in serum and were determined following the manufacturer's protocol.

Quantitative real-time PCR: qPCR was performed on cDNA from isolated mouse glomeruli using primers for Abca1, Abcg1 and APOM following standard protocols known from the prior art. Primers used: Abca1-F: CGTTTCCGGGAAGTGTCCTA/Abca1-R:GCTAGAGA-TGACAAGGAGGATGGA; Abcg1-F: AGGTCTCAGCC-TTCTAAAGTTCCTC/Abcg 1-R: TCTCTCGAAGTGAAT-GAAATTTATCG; Apom-F: CCTGGGCCTGTGGTAC-TTTA, Apom-R: CCATGTTTCCTTTCCCTTCA (SEQ ID NOs: 4-9).

Mouse models for prevention of renal disease (e.g. FIG. 3): Mice in which exon 5 of a3 chain of collagen type IV is deleted (Col4a3 KO) were obtained from the Jackson Laboratory (#002908, 129-Col4a3tm1Dec/J). Col4a3 heterozygous littermates were bred to generate Col4a3 KO mice. Three groups of mice with n=3-4 per group were studied. The three groups consisted of: 1) wildtype controls+vehicle, 2) Col4a3 KO+vehicle, and 4) Col4a3 KO+APOM. APOM was administered by weekly intraperitoneal injection starting at 4 weeks of age with 100 μg of APOM, 100 μg in week 5, 75 μg in week 6, and 67 μg in week 7. Body weight and albuminuria were monitored weekly starting at the age of 4 weeks to 16 weeks. Mice were sacrificed at 8 weeks of age when progression to end-stage renal failure had occurred.

Mouse models for treatment of renal disease (FIG. 8): Three groups of Col4a3 KO mice with n=3-4 per group were studied. The three groups consisted of: 1) wildtype controls (WT)+vehicle, 2) Col4a3 KO+vehicle, 4) Col4a3 KO+rh-APOM. rhAPOM was administered by weekly intraperitoneal injection starting at 6½ weeks of age with 100 mg of APOM per week. Body weight and albuminuria were monitored weekly starting at the age of 4 weeks to 8 weeks. Mice were sacrificed at 8 weeks of age when progression to end-stage renal failure had occurred.

Albumin/creatinine ratio: All albuminuria values are expressed as μg albumin/mg creatinine. Albumin/creatinine determined by ELISA (Bethyl Laboratories) for albumin detection and a biochemical assay based on the Jaffe method for creatinine detection (Stanbio) as previously described.

Serology: Immediately prior to sacrifice, a blood sample was collected for the determination of BUN and lipid panel analysis in the comparative laboratory core facility of the University of Miami. Serum creatinine was determined by tandem mass spectrometry (UAB-UCSD O'Brien Core Center, University of Alabama).

Mouse sacrifice surgery: Mice were perfused through the left ventricle with phosphate buffered saline at 8 weeks of age. The right kidney was removed, one pole excised and embedded in OCT, and the remainder of the kidney was used for cholesterol content determination and mRNA extraction from cortexes. The two poles of the left kidney were excised and fixed in 4% PFA, one pole was used for paraffin-embedding followed by histological analysis, other pole was post-fixed for 12 h in 4% Glutaraldehyde solution in PBS for electron microscopy.

Assessment of mesangial expansion: Periodic acid-Schiff (PAS) staining of 4 µm-thick tissue sections was performed using a standard protocol. Twenty glomeruli per section were analyzed for mesangial expansion by semi quantitative analysis (scale 0-4) performed by two blinded independent investigators.

Statistical Analysis: All in vitro experiments were performed in triplicates and 3 biological replicates were performed, in all in vivo experiments, 3-10 mice per group were analyzed. Statistical Analysis was implemented using Graph Pad Prism Software. Analysis of Variance (ANOVA) followed by Bonferroni's post test or Student's t-test was used to analyze results.

Results and Discussion

Surprisingly, lipid-induced kidney injury was observed in connection in Alport Syndrome. This role of lipid-induced kidney injury in Alport Syndrome (AS) was unexpected and had previously not been recognized. When examining mRNA (messenger ribonucleic acid) levels in glomeruli isolated from Col4a3 knockout mice (an animal model for Alport Syndrome), it was found that in addition to ABCA1, the expression of ABCG1 (ATP binding cassette subfamily G member 1) and apolipoprotein M (APOM) was also reduced in AS mice compared to controls, suggesting a possible role for A three proteins in the progression of AS. In contrast to ABCA1 and ABCG1, which are two synergistic functioning ATR-binding cassette transporter proteins, APOM is a protein which is mainly located in HDL particles where it is thought to play an important role in high-density lipoprotein (HDL) metabolism.

Figure 1B:
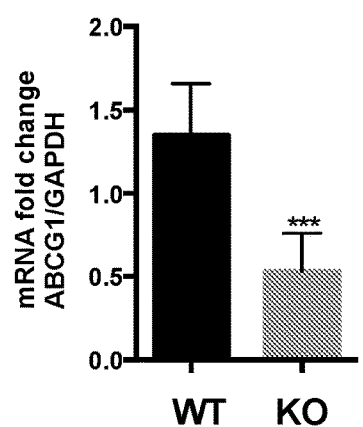
Figure 1C:
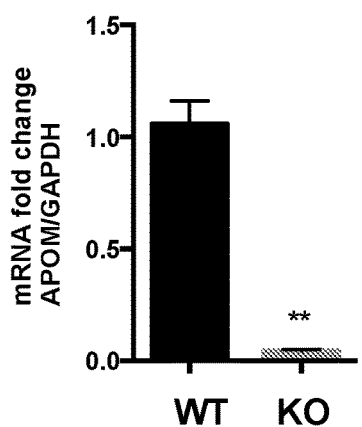
Figure 2A:
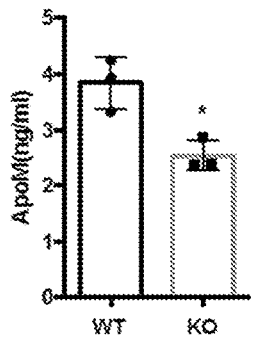
FIGS. 2A-2H: Treatment of Col4a3 knockout mice with recombinant human APOM (rh-APOM) restores normal serum levels of APOM, S1I) and triglycerides as well as S1I) content in kidney cortex and serum. (A) Bar graph analysis of APOM expression levels in kidney cortex demonstrating significantly decreased APOM expression. T-test, *$p<0.05$ (B,C) Col4a3 knockout mice show significantly increased serum levels (B) and urine (C) levels of APOM but treatment of Col4a3 knockout mice with rh-APOM restores normal serum and urine levels of APOM. T-test (serum), *$p<0.05$, F-test urine: ***$p<0.0001$. (D) Treatment of Col4a3 knockout mice with rh-APOM restores physiological serum levels of serum triglyceride content. T-test, *$p<0.05$. (E, F) Bar graph analysis of SlP expression in kidney cortex (E) and SlP serum content (F) demonstrating that treatment of Col4a3 knockout mice with rh-APOM restores physiological levels of S1P. *$p<0.05$. (G) Correlation analysis demonstrating that urine APOM levels positively correlate with albumin/creatinine ratios, R2=0.8, $p<0.01$. (H) Correlation analysis demonstrating that kidney APOM levels negatively correlate with serum creatinine levels. $R^2=0.8$, $p<0.05$.
Figure 2B:
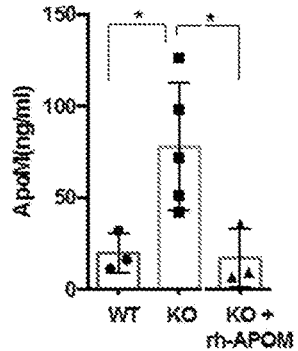
Figure 2C:
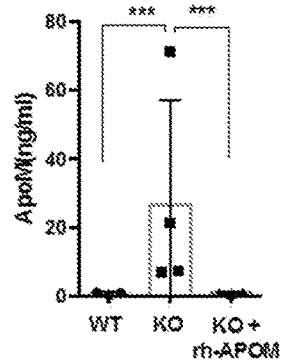
Figure 2D:
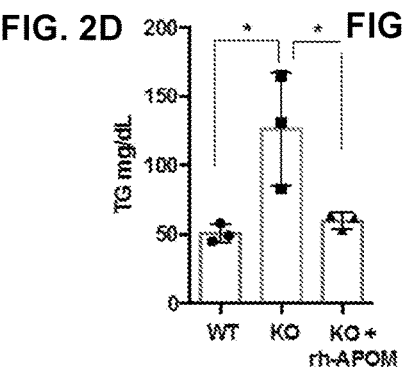
Figure 2E:
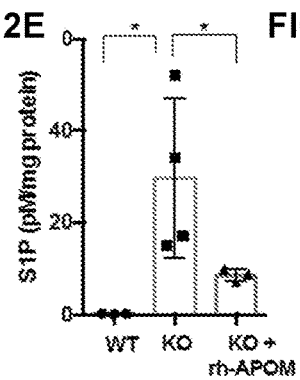
Figure 2F:
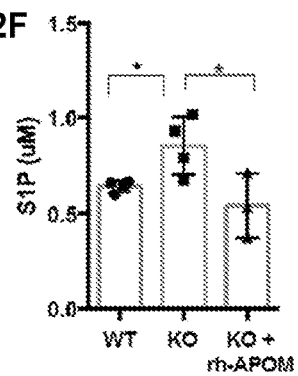
Figure 2G:
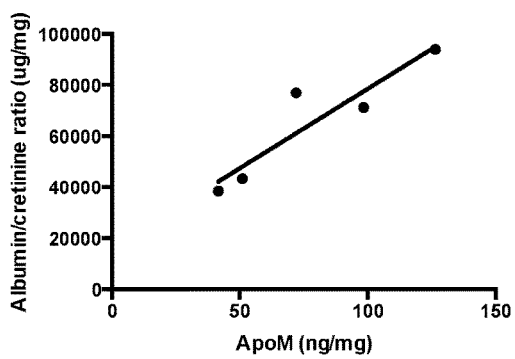
Figure 2H:
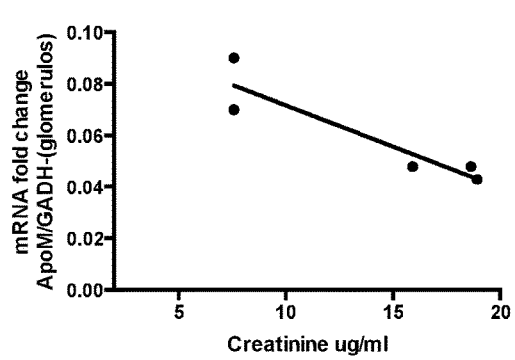
Figure 3A:
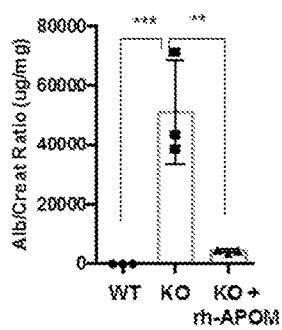
FIGS. 3A-F. Treatment of Col4a3 knockout mice with recombinant human APOM (rh-APOM) protects from renal failure. (A) rh-APOM treatment of Col4a3 knockout mice results in a significant reduction in the albumin/creatinine ratio compared to untreated Col4a3 knockout mice. $p<0.01$, *$p<0.001$. (B) Serum creatinine levels are significantly increased in Col4a3 knockout mice compared to controls. rh-APOM treatment significantly reduces serum creatinine levels in Col4a3 knockout mice. $p<0.01$. (C) Serum (Blood Urea Nitrogen) BUN levels are significantly increased in Col4a3 knockout mice compared to controls whereas rh-APOM treatment prevents increases in serum BUN levels in Col4a3 knockout mice. $p<0.01$. (D) Body weight is significantly reduced in Col4a3 knockout mice compared to controls. rh-APOM treatment prevents body weight loss in Col4a3 knockout mice$p<0.01$. (E) Treatment of Col4a3 knockout mice with rh-APOM protects from the development of glomerulosclerosis, tubular atrophy and dilation as observed in WT, WT+rhAPOM and untreated Col4a3 knockout mice. A representative image of Periodic acid Schiff stain (PAS) stained frozen kidney section is shown. (F) Bar graph analysis of the mesangial expansion score indicating that Col4a3 KO mice show a significantly increased mesangial expansion score compared to WT mice and that treatment of Col4a3 KO mice with rhAPOM significantly reduces the mesangial expansion score. T-test, *$p<0.0001$.
Figure 3B:
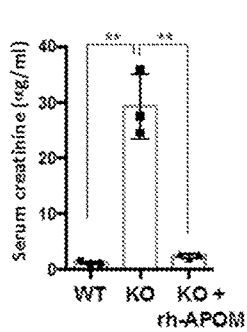
Figure 3C:
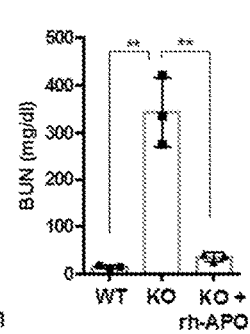
Figure 3D:
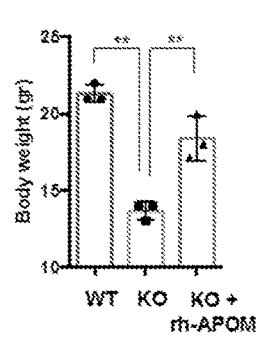
Figure 3E:
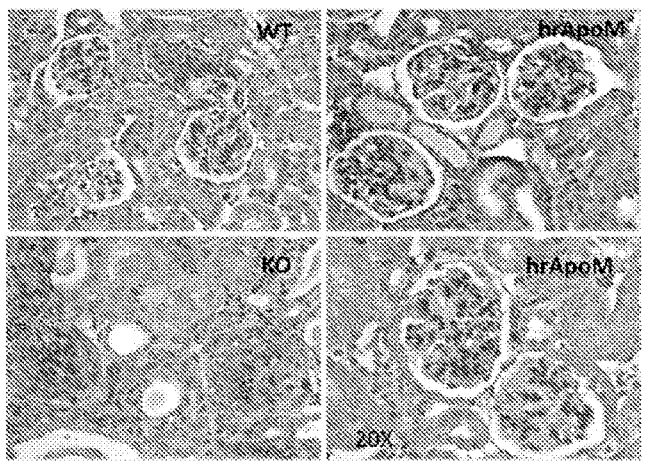
Figure 3F:
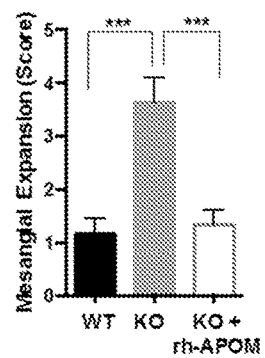

The data shown in FIG. 1 demonstrate reduced expression levels of ABCA1, ABCG1 and APOM in Col4a3 knockout mice. This correlation between aberrant expression levels and kidney injury in the animal model suggests a role of ABCA1, ABCG1 and APOM in the progression of Alport syndrome. The data of FIG. 2 further supports a role of reduced APOM expression in the progression of renal disease observed in Col4a3 knockout mice, a clinically-relevant in vivo model. Col4a3 knockout mice exhibit a combined phenotype of reduced APOM expression levels (A), reduced APOM protein levels in serum (B) and urine (C), and increased triglyceride levels in the serum (D), as well as increased Sphingosine-1-Phosphate (S1P) levels in the kidney cortex and serum. Furthermore, urinary and kidney APOM expression were found to correlate with parameters of renal function in Col4a3 KO (KO) mice (FIGS. 2G and 2H). These data suggest that APOM is necessary for regulating triglyceride levels in the serum as well as S11) levels in the kidney cortex and serum. The subsequent restoration of normal levels of S11) and triglycerides in the serum and S1P in the kidney cortex after treatment of Col4a3 knockout mice with human APOM indicates that APOM is also sufficient to treat one or more symptoms present in this clinically relevant animal model of Alport syndrome.

The data shown in FIG. 3 show that restoration of normal APOM levels by treatment with recombinant human APOM positively affected the function and structure of kidney tissue in Col4a3 knockout mice. Panels (A) to (C) show that kidney function in terms of albumin to creatinine ratios and blood urea nitrogen (BUN) levels was strongly improved in Col4a3 knockout mice treated with human APOM. Weight loss could also be prevented in Col4a3 knockout mice treated with human APOM, indicating a generally healthier metabolic state (see panel (D)). As a comparison of stained tissue slices in panel (E) demonstrates, treatment with human APOM also prevented several histological abnormalities associated with kidney injury in Alport syndrome in Col4a3 knockout mice. In particular, Col4a3 knockout mice treated with human APOM showed reduced levels of glomerulosclerosis, tubular atrophy, and dilation and mesangial expansion compared to untreated litter mates. These data indicate that treatment with human APOM can prevent the onset of functional and structural abnormalities in the kidneys of Col4a3 knockout mice, thereby protecting treated animals from renal failure.

Figure 6A:
FIGS. 6A-6N. APOM is expressed in human podocytes and human kidney biopsies and APOM deficiency in Col4a3 KO mice is associated with S1P accumulation and the activation of C signaling. (A) PCR analysis of APOM expression demonstrating that APOM is expressed in human podocytes and human kidney biopsies. P1, P2 human podocyte cell lines; H HepG2 cells (positive control); K1, K2 human kidney biopsy samples. (B) Western blot analysis demonstrating decreased APOM protein expression in Col4a3 KO mice compared to WT mice. (C) Quantitative real-time PCR analysis demonstrating significantly increased expression of SPHK1 in Col4a3 KO mice when compared to WT mice. ***$p<0.001$, t-test. (D) ELISA demonstrating significantly increased S11) levels in kidney cortex of Col4a3 KO when compared to WT mice. $p<0.05$, t-test. (E-I) Quantitative real-time PCR analysis of mRNA isolated from kidney cortexes demonstrating significantly increased expression of S1PR1 (E), S1PR2 (F), S1PR3 (G), S1PR4 (H), and S1PR5 (I) in kidney cortexes of Col4a3 KO mice when compared to WT mice. *$p<0.05$, **$p<0.01$ t-test. (J-N) Quantitative real-time PCR analysis of mRNA isolated from glomeruli demonstrating significantly increased expression of S1PR4 (M) in glomeruli of Col4a3 KO mice when compared to WT mice while the expression of S1PR1 (J), S1PR2 (K), S1PR3 (L), and S1PR5 (N) remains unchanged. *$p<0.05$, t-test.
Figure 6B:
Figure 6C:
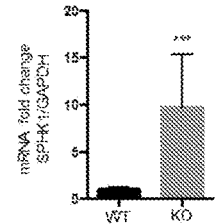
Figure 6D:
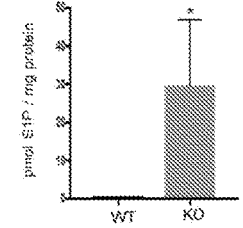
Figure 6E:
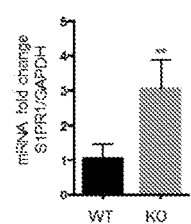
Figure 6F:
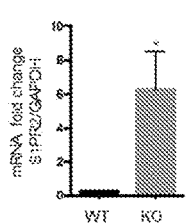
Figure 6G:
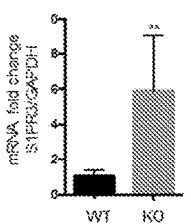
Figure 6H:
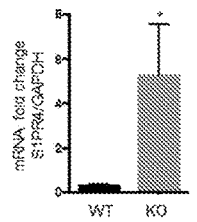
Figure 6I:
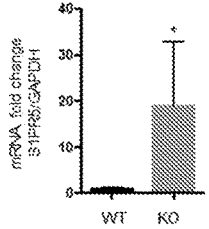
Figure 6J:
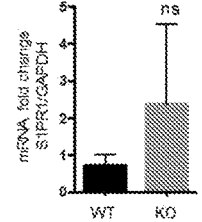
Figure 6K:
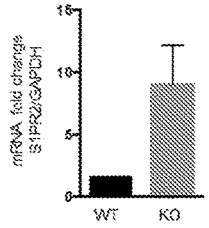
Figure 6L:
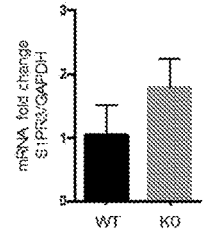
Figure 6M:
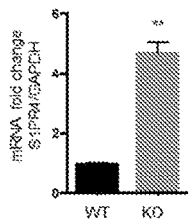
Figure 6N:
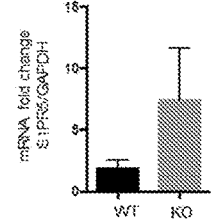
Figure 7A:
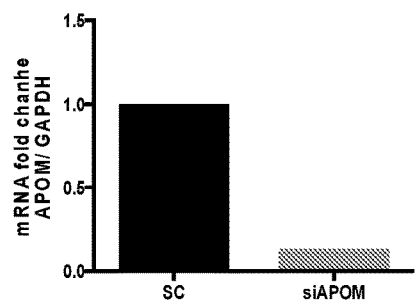
FIGS. 7A-7F. (A,B) A human podocyte cell line with stable APOM knockdown was established by lentiviral infection. Quantitative real-time PCR (A) and Western blot analysis (B) were performed demonstrating a 75% knockdown of APOM mRNA and protein expression in siAPOM compared to scramble infected (SC) podocytes. n=1. (C) Western blot analysis demonstrating decreased RhoA expression in siAPOM podocytes when compared to SC podocytes. (D) Bar graph analysis demonstrating significantly decreased ABCC1 expression in siAPOM compared to SC podocytes as established by quantitative real-time PCR. Triplicate, n=1. (E) The expression of different integrin subunits was determined using quantitative real-time PCR. Bar graph analysis demonstrating increased expression of ITGB3 in siAPOM compared to SC podocytes. Triplicate, n=1. (F) Bar graph analysis demonstrating increased apoptosis in an S1P-dependent manner in S11)+Albumin treated when compared to S1P+APOM treated podocytes. Triplicate, n=1.
Figure 7B:
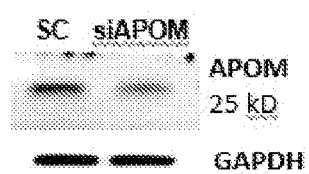
Figure 7C:
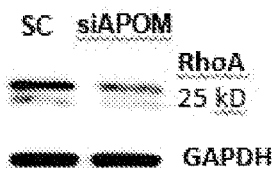
Figure 7D:
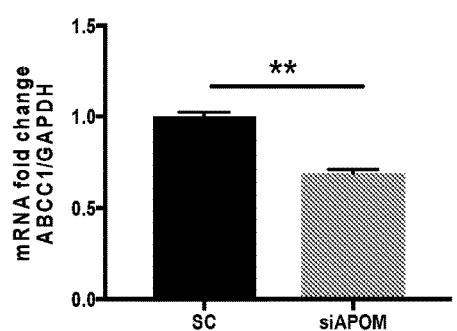
Figure 7E:
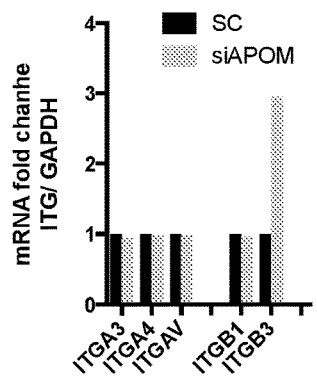
Figure 7F:
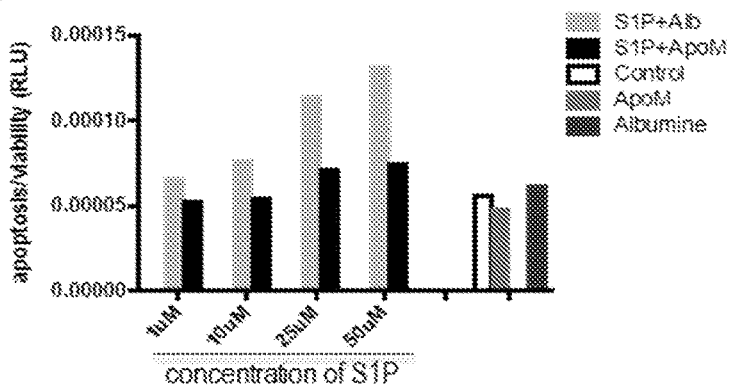

The data shown in FIG. 6A-6N show that APOM is expressed in human podocytes and human kidney biopsies and APOM deficiency in Col4a3 KO mice is associated with S11) accumulation and the activation of C signaling.

The data shown in FIG. 7 show a human podocyte cell line with stable APOM knockdown (siAPOM) established by lentiviral infection (FIG. 7A-7B) and demonstrates decreased RhoA protein expression (FIG. 7C) and ABCC1 mRNA expression in siAPOM podocytes (FIG. 7D) versus scrambled controls. In addition, increased expression of ITGB3 was detected in siAPOM versus scrambled controls (FIG. 7E). Representative images acquired using the OPERA high content screening system after labeling of intracellular lipids with Nile Red and cell mask and phalloidin to visualize cells. Increased lipid droplets were detected in a dose-dependent manner in S11)+albumin treated podocytes, whereas a similar increase was not detected in podocytes that were treated with S11)+APOM (data not shown). Increased apoptosis was detected in an S1P-dependent manner in S11)+Albumin treated when compared to S11)+APOM treated podocytes (FIG. 7F).

Figure 8A:
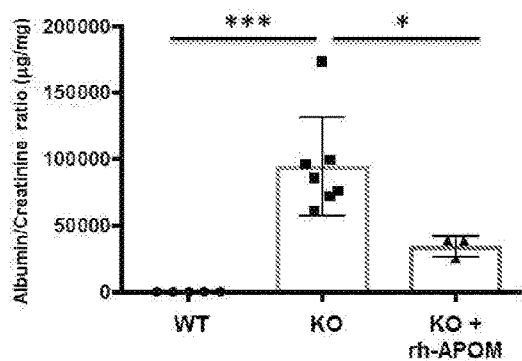
FIGS. 8A-8B. Treatment of Col4a3 knockout (KO) mice with recombinant human APOM (rh-APOM) improves established renal failure. (A) rh-APOM treatment of Col4a3 knockout mice results in a significant reduction in the albumin/creatinine ratio and (B) plasma creatinine levels compared to untreated Col4a3 knockout mice. *$p<0.05$, ***$p<0.001$.
Figure 8B:
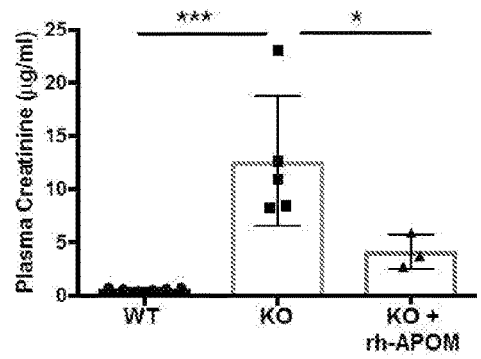

The data shown in FIG. 8 demonstrates that treatment of Col4a3 knockout (KO) mice 6½ weeks of age with recombinant human APOM (rh-APOM) improved established renal failure. In this case mice have developed clinical signs of renal disease (proteinuria) and are treated with rh-APOM. rh-APOM treatment of Col4a3 knockout mice (KO) resulted in a significant reduction in the albumin/creatinine ratio (FIG. 8A) and plasma creatinine levels compared to untreated Col4a3 knockout mice (FIG. 8B).

The data described herein demonstrate that administration of APOM to an in vivo model of Alport Syndrome (Col4a3 mice) protected against renal failure and abnormal lipid content in kidney cortexes. Treated animals also had healthier body weights and better kidney function. The example demonstrates a role of APOM in the mechanism underlying Alport syndrome and provides evidence for the therapeutic use of APOM in treating or preventing kidney disease.

What is claimed is:

1. A method of treating chronic kidney disease in a subject suffering from albuminuria or proteinuria, the method comprising administering human apolipoprotein M in an amount effective to treat chronic kidney disease in the subject.

2. A method of treating or preventing renal disease in a subject having mutations in one or more of genes Col4a3, Col4a4, or Col4a5, the method comprising administering human apolipoprotein M to the subject in an amount effective to treat or prevent the renal disease in the subject.

3. A method of preventing chronic kidney disease in a subject having mutations in one or more of genes Col4a3, Col4a4, or Col4a5, the method comprising administering human apolipoprotein M to the subject.

* * * * *